United States Patent [19]
Mizutani et al.

[11] 3,969,393
[45] July 13, 1976

[54] PROCESS FOR PREPARING CYCLOPROPANE-CARBOXYLIC ACID ESTERS

[75] Inventors: Toshio Mizutani; Yoshitaka Ume, both of Toyonaka; Takashi Matsuo, Nishinomiya, all of Japan

[73] Assignee: Sumitomo Chemical Company, Limited, Osaka, Japan

[22] Filed: Aug. 6, 1974

[21] Appl. No.: 495,154

[30] Foreign Application Priority Data
Aug. 6, 1973 Japan..........................48-88674
Aug. 23, 1973 Japan..........................48-94980

[52] U.S. Cl....................... 260/468 H; 260/297 R; 260/567.6 H
[51] Int. Cl.²......................................... C07C 67/00
[58] Field of Search............................... 260/468 H

[56] References Cited
OTHER PUBLICATIONS
Williams et al., Synthesis 1974, 727.

*Primary Examiner*—Robert Gerstl
*Attorney, Agent, or Firm*—Sughrue, Rothwell, Mion, Zinn & Macpeak

[57] ABSTRACT

A process for preparing an organic acid ester of the formula (I),

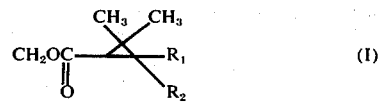

wherein $R_1$ is a hydrogen atom or a methyl group, $R_2$ is a methyl group, a vinyl group, a 2,2-dichlorovinyl group, a 1-propenyl group, a 2-methyl-1-propenyl group, a 2-carbomethoxy-1-propenyl group, a 2-methoxymethyl-1-propenyl group, a 1,3-butadienyl group, a 2-methyl-1,3-butadienyl group or a cyclopentylidenemethyl group when $R_1$ is a hydrogen atom, and $R_2$ is a methyl group when $R_1$ is a methyl group; which comprises reacting an acid of the formula (II),

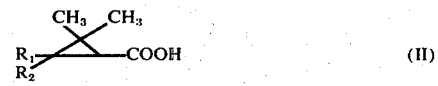

wherein $R_1$ and $R_2$ are each as defined above, or its reactive derivative, or mixture of the acid and its reactive derivative with a quaternary ammonium salt of the formula (III),

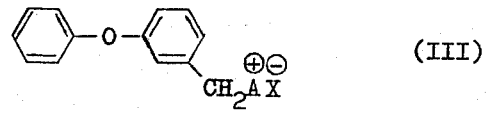

wherein X is a halogen atom, A is an alkylamine, pyridine or an N-alkylaniline.

6 Claims, No Drawings

PROCESS FOR PREPARING CYCLOPROPANE-CARBOXYLIC ACID ESTERS

BACKGROUND OF THE INVENTION

1. Field of the Invention

The present invention relates to a process for preparing cyclopropane-carboxylic acid esters comprising preparing quaternary ammonium salts from organohalide compounds and amines, and then preparing the esters from the resulting amine salts.

2. Description of the Prior Art

The 3-phenoxybenzyl cyclopropane carboxylates of the general formula (I) are known compounds as disclosed in Japanese Patent Publication No. 21473/1971 and have utility as excellent insecticides with low toxicity.

SUMMARY OF THE INVENTION

An object of the present invention is to provide an industrially advantageous process for producing the excellent, low-toxic insecticides of the formula (I).

The present invention provides a process for preparing 3-phenoxybenzyl cyclopropane carboxylates of the formula (I),

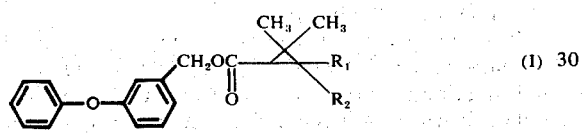

wherein $R_1$ is a hydrogen atom or a methyl group, $R_2$ is a methyl group when $R_1$ is a methyl group; and $R_2$ is a methyl group, a vinyl group, a 2,2-dichlorovinyl group, a 1-propenyl group, a 2-methyl-1-propenyl group, a 2-carbomethoxy-1-propenyl group, a 2-methoxymethyl-1-propenyl group, a 1,3-butadienyl group, a 2-methyl-1,3-butadienyl group or a cyclopentylidenemethyl group when $R_1$ is a hydrogen atom; comprising reacting a quaternary ammonium salt of the formula (III),

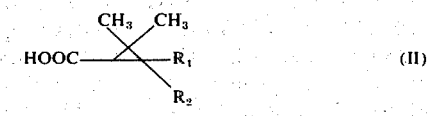

wherein X is a halogen atom and A is an alkylamine, pyridine or an N-alkylaniline with a cyclopropane-carboxylic acid of the formula (II),

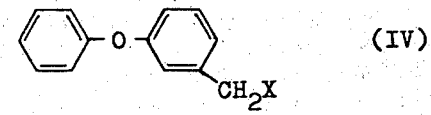

wherein $R_1$ and $R_2$ each is as defined above; with a mixture of the cyclopropane carboxylic acid and a reactive derivative thereof, e.g., the alkali metal salt, the ammonium salt or the alkyl-ammonium salt of the cyclopropane carboxylic acid; or with a reactive derivative thereof, e.g., the alkali metal salt, the ammonium salt or the alkylammonium salt of the cyclopropane carboxylic acid.

An embodiment includes preparing the quaternary ammonium salt of the general formula (III), e.g., a 3-phenoxybenzyl alkyl-ammonium halide, a 3-phenoxybenzyl pyridinium halide or a 3-phenoxybenzyl alkylarylammonium halide, as a useful intermediate of insecticides by reacting a 3-phenoxybenzyl halide of the general formula (IV),

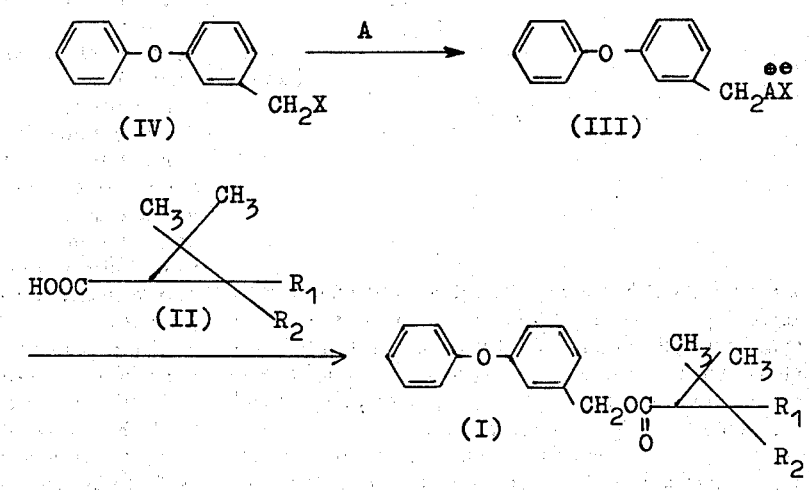

wherein X is a halogen atom with an alkylamine, pyridine or an N-alkylaniline.

DETAILED DESCRIPTION OF THE INVENTION

The reaction process of this invention can be schematically shown as follows:

wherein X is a halogen atom, A is an alkylamine, pyridine or an N-alkylaniline, and $R_1$ and $R_2$ each is as defined above.

By studying an industrially advantageous preparation of the 3-phenoxybenzyl ester of cyclopropane-carboxylic acid of the formula (I), a method has been found in which the 3-phenoxybenzyl halide could be obtained in a high yield by halogenating the side chain of m-tolylphenylether. However, this reaction produces by-products such as 3-phenoxybenzalhalide and derivatives containing a nuclear halogen atom, in addition to the desired 3-phenoxybenzyl halide, and the resulting products are obtained as a mixture together with the starting materials. The direct isolation of the 3-phenoxybenzyl halide from the mixture obtained by fractional distillation is very difficult due to the low thermal stability of the desired 3-phenoxybenzyl halide and the by-products as well as staining and corrosion of the apparatus. In general, therefore, the isolation by fractional distillation is carried out after the components of the mixture are converted to more chemically stable derivatives, such as after acetylation. However, for example, 3-phenoxybenzyl acetate has such a high boiling point (147° – 150°C/1mmHg) that the fractional distillation on an industrial scale is very limited instrumentally and thus becomes necessarily inefficient. Therefore, the discovery of an industrially advantageous separation of the 3-phenoxybenzyl halide from the mixture has been desired.

The method of separation of the 3-phenoxybenzyl halide without this disadvantage and which is capable of mass production has been studied, and a new process in which the compound can be separated from the reaction mixture, with ease and high purity, by converting the compound to a quaternary ammonium salt or the pyridinium salt has been found. That is, the 3-phenoxybenzyl halide can be separated, in the form of crystals of the salts or aqueous solutions of the salts, from the organic layer which contains dissolved impurities. The quaternary ammonium salt and the pyridinium salt of the 3-phenoxybenzyl halide represented by the formula,

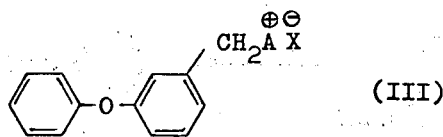

(III)

wherein A and X are each as defined above, obtained according to the present invention are new compounds from which the desired final products, that is, the 3-phenoxybenzyl esters of cyclopropane-carboxylic acid can be obtained easily, directly and in a high yield according to the following methods:

1. A method comprising reacting the quaternary ammonium salt or the pyridinium salt of the formula (III) with the free acid of the formula (II) or with the alkali metal salt, ammonium salt or alkylammonium salt of the free acid of the formula (II), or with a mixture of the alkali metal salt, the ammonium salt or the alkylammonium salt of the free acid of the formula (II) and the free acid of the formula (II).

2. A method comprising converting the quaternary ammonium salt or the pyridinium salt of the formula (III) to the acetate by reaction with sodium acetate, hydrolyzing the resulting acetate to 3-phenoxybenzyl alcohol, and then reacting the alcohol with the acid chloride of the cyclopropane-carboxylic acid of the formula (II).

3. A method comprising hydrolyzing the quaternary ammonium salt or the pyridinium salt of the formula (III) in dimethylformamide to 3-phenoxybenzyl alcohol, and then reacting the resulting alcohol with the acid chloride of the cyclopropane-carboxylic acid of the formula (II).

As the halogen atom of the 3-phenoxybenzyl halides (IV) used according to the present invention, chlorine and bromine atoms are suitable. The benzyl halides can contain starting materials and various halogen derivatives obtained, as by-products, by halogenation of m-tolylphenyl ether and unchanged m-tolylphenyl ether, based on the characteristics of the present invention. Examples of the other starting materials, that is, the alkylamine, the N-alkylaniline or pyridine, are exemplified by triethylamine, trimethylamine, diethylaniline, dimethylaniline, and pyridine, and from an industrial point of view, triethylamine, diethylaniline, dimethylaniline and pyridine are preferred. The amount of the tertiary amine used is preferably 1.1 to 2 times on a molar basis to the halide.

The quaternary salt can be formed by reacting the 3-phenoxybenzyl halide with an alkylamine, an N-alkylaniline or pyridine in inert solvents such as diethyl ether, benzene, toluene, xylene and chlorobenzene, at room temperature (e.g., about 20° – 30°C) or, if desired, up to the boiling point of the solvent. A preferred reaction temperature is 70° to 80°C.

The preparation of the ester compounds in the present invention will be illustrated in greater detail as follows.

The esters of the formula (I) can be obtained by reacting the quaternary ammonium salt or pyridinium salt of the 3-phenoxybenzyl halide (III) with the cyclopropane-carboxylic acid (II) in a suitable inert solvent such as dimethylformamide, acetone, methyl isobutyl ketone, anisole, toluene, xylene, chlorobenzene or nitrobenzene. In the reaction, heating is preferred to accelerate the reaction. A part of the cyclopropane-carboxylic acid (II) can be added in the form of its alkali metal salt (for example, the sodium or potassium salt), ammonium salt or alkyl-ammonium salt (for example, the triethyl ammonium salt), also with the free acid to accelerate the anion exchange reaction with the quaternary salt of the 3-phenoxybenzyl halide (III). Conversion of all of the acid of the formula (II) to its salt is also satisfactory. All or a part of the acid can be converted to its salt in the esterification reaction in situ, if desired.

Examples of the quaternary salts of the 3-phenoxybenzyl halide (III) which can be used in the present invention are exemplified as follows.

3-Phenoxybenzyl triethyl ammonium chloride
3-Phenoxybenzyl triethyl ammonium bromide
3-Phenoxybenzyl dimethylphenyl ammonium bromide
3-Phenoxybenzyl diethylphenyl ammonium bromide
3-Phenoxybenzyl pyridinium chloride
3-Phenoxybenzyl pyridinium bromide These salts can be obtained by reacting the reaction mixture obtained after halogenation of the m-tolylphenyl ether with an alkylamine, an alkylarylamine or pyridine in an inert solvent such as benzene or toluene, and then filtering the resulting salt crystals or separating the salt in a form of an aqueous solution from the organic layer, and followed by evaporation to dryness if desired.

Illustrative examples of cyclopropane carboxylic acids of the formula (II) are exemplified as follows.
Chrysanthemic acid
Pyrethric acid
2,2,3-Trimethyl-cyclopropane-carboxylic acid
2,2,3,3-Tetramethyl-cyclopropane-carboxylic acid
2,2-Dimethyl-3-vinyl-cyclopropane-carboxylic acid
2,2-Dimethyl-3-(2',2'-dichlorovinyl)-cyclopropane-carboxylic acid
2,2-Dimethyl-3-(1'-propenyl)-cyclopropane-carboxylic acid
2,2-Dimethyl-3-(2'-methoxymethyl-1'-propenyl)-cyclopropane-carboxylic acid
2,2-Dimethyl-3-(1',3'-butadienyl)-cyclopropane-carboxylic acid
2,2-Dimethyl-3-(2'-methyl-1',3'-butadienyl)-cyclopropane-carboxylic acid
2,2-Dimethyl-3-(cyclopentylidenemethyl)-cyclopropane-carboxylic acid The process for preparing compounds within the scope of the present invention are illustrated in greater detail by reference to the following examples, which are only illustrative and are not intended to be construed as limiting the scope of the present invention.

EXAMPLE 1

37.5 g of the brominated product of m-tolylphenyl ether containing 26.3 g of 3-phenoxybenzyl bromide was mixed with 100 ml of toluene, and then a solution of 15.1 g of triethylamine in 30 ml of toluene was added dropwise thereto. After the addition, the mixture was maintained at 90° to 100°C for 1 hour while stirring and then cooled. The separated crystals were filtered out, washed with toluene and then dried under a reduced pressure to obtain 35.8 g of 3-phenoxybenzyl triethyl ammonium bromide (m.p. 160° – 163°C).

| I.R. $\nu_{max}^{Nujol}$ | 1575, 1475, 1240, 1210, 1160, 990, 810, 790, 750 cm$^{-1}$ | | | |
|---|---|---|---|---|
| Elementary analysis: | | | | |
| | C | H | N | Br |
| Found (%) | 62.90 | 7.36 | 3.80 | 22.35 |
| Calculated (%) (as $C_{19}H_{26}ONBr$) | 62.64 | 7.19 | 3.84 | 21.93 |

EXAMPLE 2

52.6 g of the brominated product of m-tolylphenyl ether containing 26.3 g of 3-phenoxybenzyl bromide was added to a mixed solution of 100 ml of xylene and 50 ml of water, and then 11.9 g of pyridine was added thereto. The mixture was heated to 70° to 75°C, kept at the same temperature for 3 hours while stirring and then cooled to room temperature (about 20° – 30°C). The lower aqueous layer which separated was removed, washed with a small amount of xylene, evaporated and then dried under a reduced pressure to obtain 34.5 g of colorless, crystalline 3-phenoxybenzyl pyridinium bromide (m.p. 120° – 121°C).

| Elementary analysis: | C | H | N | Br |
|---|---|---|---|---|
| Found (%) | 63.21 | 4.70 | 4.10 | 23.37 |
| Calculated (%) (as $C_{18}H_{16}ONBr$) | 63.17 | 4.71 | 4.09 | 23.35 |

EXAMPLE 3

18.2 g of the chlorinated product of m-tolylphenyl ether containing 13.2 g of 3-phenoxybenzyl chloride was treated with a solution of 9.1 g of triethylamine in 60 ml of benzene in the same manner as described in Example 1. Thus, 17.8 g of colorless, needle-like 3-phenoxybenzyl triethyl ammonium chloride was obtained (hygroscopic, no clear m.p.).

| I.R. $\nu_{max}^{Nujol}$ | 1590, 1490, 1380, 1255, 1220, 1070, 1080, 1000, 830, 770 cm$^{-1}$ | | | |
|---|---|---|---|---|
| Elementary analysis: | | | | |
| | C | H | N | Cl |
| Found (%) | 71.05 | 8.52 | 4.17 | 10.91 |
| Calculated (%) (as $C_{19}H_{26}ONCl$) | 71.34 | 8.19 | 4.38 | 11.08 |

EXAMPLE 4

The same procedures were carried out in the same manner as described in Example 3, except that 7.2 g of pyridine was used in place of 9.1 g of triethylamine. Thus, 14.5 g of colorless, amorphous 3-phenoxybenzyl pyridinium chloride was obtained (hygroscopic, no clear m.p.).

| I.R. $\nu_{max}^{Nujol}$ | 1630, 1590, 1490, 1260, 1210, 1170, 1150, 780, 740, 690 cm$^{-1}$ | | | |
|---|---|---|---|---|
| Elementary analysis: | | | | |
| | C | H | N | Cl |
| Found (%) | 72.45 | 5.60 | 4.55 | 11.37 |
| Calculated (%) (as $C_{18}H_{16}ONCl$) | 72.60 | 5.42 | 4.70 | 11.91 |

EXAMPLE 5

7.3 g of 3-phenoxybenzyl triethyl ammonium bromide was mixed with 50 ml of dimethylformamide and then 4.2 g of sodium d,l-cis,trans-chrysanthemate was added thereto at room temperature. The mixture was heated under reflux for 5 hours while stirring, and then cooled. After adding 200 ml of water, the reaction solution was extracted with benzene, and the benzene layer was washed successively with dilute aqueous hydrochloric acid, a saturated aqueous sodium chloride solution, a saturated aqueous sodium bicarbonate solution and a saturated aqueous sodium chloride solution, and then dried over anhydrous magnesium sulfate. Removal of benzene under reduced pressure gave 6.35 g of 3-phenoxybenzyl-d,l-cis,trans-chrysanthemate ($n_D^{25}$ 1.5485).

EXAMPLE 6

After 5.5 g of 3-phenoxybenzyl triethyl ammonium bromide was mixed with 50 ml of toluene, 3.4 g of sodium d-cis,trans-chrysanthemate was added thereto. The mixture was heated for 16 hours while stirring, cooled, and then poured into 100 ml of water. The organic layer was separated and the aqueous layer was extracted with toluene and then the combined organic layer was treated in the same manner as described in Example 5 to obtain 4.4 g of 3-phenoxybenzyl d-cis,-trans-chrysanthemate ($n_D^{27}$ 1.5482).

$[\alpha]_D^{25} = -11.1°$ (c = 3%, CHCl$_3$). Trans : cis = 8 : 2 molar ratio.

EXAMPLE 7

After 4.8 g of 3-phenoxybenzyl triethyl ammonium chloride was mixed with 30 ml of dimethylformamide, 2.55 g of 2,2,3,3-tetramethyl-cyclopropane-carboxylic acid was added thereto. Then 2.3 g of triethylamine was added dropwise thereto, and the resulting mixture was stirred at room temperature for 1 hour, heated under reflux for 8 hours while stirring and then cooled. After adding 100 ml of water, the reaction solution was extracted with diethyl ether and then the ether layer was treated in the same manner as described in Example 5 to obtain 4.4 g of 3'-phenoxybenzyl 2,2,3,3-tetramethyl-cyclopropane-carboxylate ($n_D^{26}$ 1.5463).

EXAMPLE 8

6.7 g of 3-phenoxybenzyl triethyl ammonium bromide, 3.8 g of sodium 2,2-dimethyl-3-vinylcyclopropane-carboxylate and 70 ml of dimethylformamide were treated in the same manner as described in Example 5. Thus 5.7 g of 3'-phenoxybenzyl 2,2-dimethyl-3-vinyl-cyclopropane-carboxylate was obtained ($n_D^{27}$ 1.5520).

EXAMPLE 9

5.9 g of 3-phenoxybenzyl pyridinium chloride, 1.0 g of 2,2,3-trimethyl-cyclopropane-carboxylic acid, 1.1 g of sodium 2,2,3-trimethyl-cyclopropane-carboxylate and 50 ml of methyl isobutyl ketone were treated in the same manner as described in Example 6 to obtain 4.1 g of 3'-phenoxybenzyl 2,2,3-trimethyl-cyclopropane-carboxylate ($n_D^{25}$ 1.5435).

EXAMPLES 10 TO 16

A mixture of 0.02 mole of 3-phenoxybenzyl triethyl ammonium bromide, 0.022 mole of sodium cyclopropane-carboxylate as shown in Table 1 and 70 ml of dimethylformamide was heated under reflux for 8 hours while stirring and then treated according to Example 5. The results obtained are shown in Table 1.

Table 1

| Example No. | Sodium Carboxylate Used | Carboxylic Acid Ester Obtained Name | Yield (%) | Refractive Index ($n_D^{25}$) |
|---|---|---|---|---|
| 10 | Sodium 2,2-dimethyl-3-(2'-methoxymethyl-1'-propenyl)-cyclopropane-carboxylate | 3-Phenoxybenzyl 2',2'-dimethyl-3'-(2''-methoxymethyl-1'''-propenyl)-cyclopropane-carboxylate | 87 | 1.5445 |
| 11 | Sodium 2,2-dimethyl-3-(cyclopentylidenemethyl)-cyclopropane-carboxylate | 3-Phenoxybenzyl 2',2'-dimethyl-3'-(cyclopentylidenemethyl)-cyclopropane-carboxylate | 90 | 1.5512 |
| 12 | Sodium 2,2-dimethyl-3-(2'-methyl-1',3'-butadienyl)-cyclopropane-carboxylate | 3-Phenoxybenzyl 2',2'-dimethyl-3'-(2''-methyl-1''',3''-butadienyl)-cyclopropane-carboxylate | 88 | 1.5719 |
| 13 | Sodium 2,2-dimethyl-3-(1',3'-butadienyl)-cyclopropane-carboxylate | 3-Phenoxybenzyl 2',2'-dimethyl-3'-(1'',3''-butadienyl)-cyclopropane-carboxylate | 89 | 1.5660 |
| 14 | Sodium 2,2-dimethyl-3-(1'-propenyl)-cyclopropane-carboxylate | 3-Phenoxybenzyl 2',2'-dimethyl-3'-(1''-propenyl)-cyclopropane-carboxylate | 88 | 1.5472 |
| 15 | Sodium 2,2-dimethyl-3-(2'-carbomethoxy-1'-propenyl)-cyclopropane-carboxylate | 3-Phenoxybenzyl 2',2'-dimethyl-3'-(2''-carbomethoxy-1''-propenyl)-cyclopropane-carboxylate | 85 | 1.5610 |
| 16 | Sodium 2,2-dimethyl-3-(2',2'-dichlorovinyl)-cyclopropane-carboxylate | 3-Phenoxybenzyl 2',2'-dimethyl-3'-(2'',2''-dichlorovinyl)-cyclopropane-carboxylate | 88 | 1.5627 |

While the invention has been described in detail and with reference to specific embodiments thereof, it will be apparent to one skilled in the art that various changes and modifications can be made therein without departing from the spirit and scope thereof.

What is claimed is:

1. A process for preparing an organic acid ester of the formula (I),

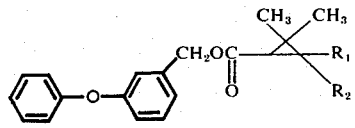

wherein R$_1$ is a hydrogen atom or a methyl group, R$_2$ is a methyl group, a vinyl group, a 2,2-dichlorovinyl group, a 1-propenyl group, a 2-methyl-1-propenyl group, a 2-carbomethoxy-1-propenyl group, a 2-methoxymethyl-1-propenyl group, a 1,3-butadienyl group, a 2-methyl-1,3-butadienyl group or a cyclopentylidenemethyl group when R$_1$ is a hydrogen atom, and R$_2$ is a methyl group when R$_1$ is a methyl group; which comprises reacting an acid of the formula (II).

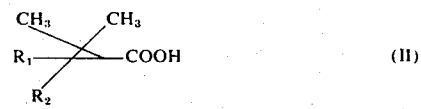

wherein R$_1$ and R$_2$ are each as defined above, or its reactive derivative, or a mixture of the acid and its reactive derivative wherein said reactive derivative is selected from the group consisting of the alkali metal salt, ammonium salt and alkylammonium salt of the acid of formula (II), with a quaternary ammonium salt of the formula (III)

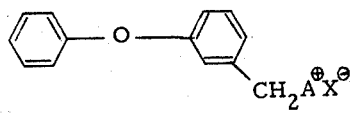

(III)

wherein X is a halogen atom, and A is an alkylamine, pyridine or an N-alkylaniline wherein said reacting is in the presence of a solvent selected from the group consisting of dimethylformamide, acetone, methyl isobutyl ketone, anisole, toluene, xylene, chlorobenzene and nitrobenzene and is conducted at a temperature lower than the boiling point of the solvent used and wherein the molar ratio of said quaternary ammonium salt to said acid or acid reactive derivative is between 1:0.76 to 1:1.27.

2. The process according to claim 1, including preparing the quaternary ammonium salt (III) by reacting a 3-phenoxybenzyl halide of the formula (IV),

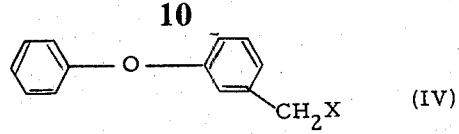

(IV)

wherein X is a halogen atom with an amine selected from the group consisting of an alkylamine, pyridine and an N-alkylaniline wherein the molar ratio of the amine to the 3-phenoxybenzyl halide of formula (IV) is 1.1:1 to 2:1 and wherein said reacting to prepare said quaternary ammonium salt (III) is in the presence of a solvent selected from the group consisting of diethyl ether, benzene, toluene, xylene and chlorobenzene and is carried out at a temperature between room temperature and the boiling point of the solvent used.

3. The process according to claim 2, wherein the halogen atom is a chlorine atom or a bromine atom.

4. The process according to claim 2, wherein the amine is a member selected from the group consisting of triethylamine, trimethylamine, diethylaniline, dimethylaniline and pyridine.

5. The process according to claim 2, wherein the reacting is between 70° to 80°C.

6. The process according to claim 1, wherein the organic acid ester is 3-phenoxybenzyl-2',2'-dimethyl-3'-(2'',2''-dichlorovinyl)-cyclopropanecarboxylate.

* * * * *